United States Patent [19]

Shanklin, Jr. et al.

[11] 4,313,949
[45] Feb. 2, 1982

[54] METHOD OF PRODUCING AN INHIBITORY EFFECT ON BLOOD PLATELET AGGREGATION

[75] Inventors: James R. Shanklin, Jr.; Dwight A. Shamblee; David A. Walsh, all of Richmond, Va.

[73] Assignee: A. H. Robins Company, Inc., Richmond, Va.

[21] Appl. No.: 234,532

[22] Filed: Feb. 17, 1981

Related U.S. Application Data

[62] Division of Ser. No. 78,860, Sep. 26, 1979.

[51] Int. Cl.$^3$ ............... A61K 31/535; A61K 31/165
[52] U.S. Cl. ..................... 424/248.56; 424/248.5; 424/248.52; 424/250; 424/267; 424/274; 424/324
[58] Field of Search .......... 424/248.5, 248.52, 248.56, 424/250, 267, 274, 324

[56] References Cited

U.S. PATENT DOCUMENTS 4,045,576 8/1977 Welstead et al. ................. 424/309

Primary Examiner—John M. Ford
Assistant Examiner—R. W. Ramsuer

[57] ABSTRACT

Novel 2-amino-3-benzoyl-phenylacetamides are provided having the formula:

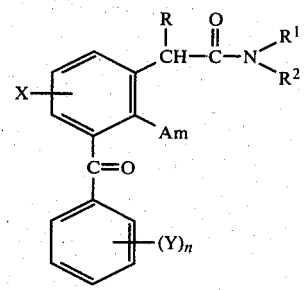

wherein R represents hydrogen or lower alkyl, $R^1$ and $R^2$ represent hydrogen, lower alkyl, cycloalkyl, phenyl and phenyl substituted by lower alkyl, lower alkoxy, halogen, nitro and trifluoromethyl, and $R^1$ and $R^2$ when taken together with the adjacent nitrogen may form a heterocyclic residue; X represents hydrogen, lower alkyl, lower alkoxy, halogen or trifluoromethyl; Y represents hydrogen, lower alkyl, lower alkoxy, halogen, trifluoromethyl, lower alkylthio, lower alkyloxythio or lower alkyldioxythio; Am is primary amino ($-NH_2$), methylamino or dimethylamino, and n is 1 to 3 inclusive. The compounds exhibit anti-inflammatory, antipyretic, anti-blood platelet aggregation and analgetic pharmacological activities.

9 Claims, No Drawings

METHOD OF PRODUCING AN INHIBITORY EFFECT ON BLOOD PLATELET AGGREGATION

This is a division, of application Ser. No. 078,860, filed Sept. 26, 1979 pending.

BACKGROUND OF THE INVENTION

1. Field of Invention

The present invention is concerned with certain novel 2-amino-3-benzoylphenylacetamides and heterocyclic derivatives thereof and pharmacological methods of treatment, pharmaceutical compositions and use thereof and methods of producing the same. The compounds are anti-inflammatory, antipyretic, analgetic and blood-platelet-aggregation inhibiting agents which exhibit minimal undesirable side effects of gastric irritation on oral administration to living animal bodies.

2. Description of the Prior Art

2-Amino-3-benzoylphenylacetic acids, esters and metal salts thereof having anti-inflammatory activity and blood-platelet-aggregating inhibition properties are disclosed in U.S. Pat. No. 4,045,576.

South African Pat. No. 68/4682 discloses benzoylphenylacetamides generically having a variety of substituents in indefinite positions on phenyl. None of the specific compounds disclosed therein are aminophenylacetamides.

Generally, in the past, strong anti-inflammatory drugs have been found to produce serious side effects of gastric bleeding and ulceration when administered orally to animals in the effective range. The compounds of the present invention have been found to have the advantage that extremely low incidence of gastric irritation is observed when administered in the range effective for reducing inflammation as compared to indomethacin and the less irritating 2-amino-3-benzoylphenylacetic acids disclosed in U.S. Pat. No. 4,045,576.

OBJECTS AND SUMMARY OF THE INVENTION

The compounds of the present invention are 2-amino-3-benzoylphenylacetamides illustrated generally by the following formula:

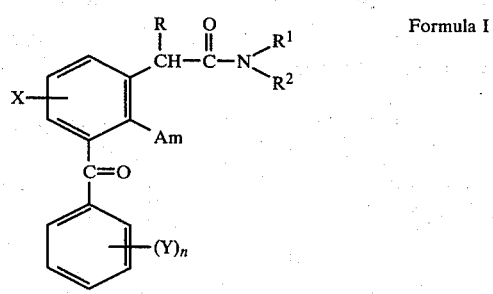

Formula I wherein R is hydrogen and lower alkyl; $R^1$ and $R^2$ are hydrogen, lower alkyl, cycloalkyl, phenyl and phenyl substituted by lower alkyl, lower alkoxy, halogen, nitro and trifluoromethyl, and $R^1$ and $R^2$ taken together with the adjacent nitrogen may form a heterocyclic residue; X is hydrogen, lower alkyl, lower alkoxy, halogen and trifluoromethyl; Y is hydrogen, lower alkyl, lower alkoxy, halogen, trifluoromethyl, lower alkylthio, lower alkyloxythio and lower alkyldioxythio; Am is primary amino ($-NH_2$), methylamino or dimethylamino, and n is 1–3 inclusive.

The novel compounds of Formula I possess valuable pharmacological properties and are useful when administered internally in effective amount in alleviating inflammation, alleviating pain in an animal afflicted with pain, inhibiting blood-platelet aggregation and combating temperature elevation in living animal bodies but with minimal side effects as compared to some other strong anti-inflammatory agents. Illustrative of the anti-inflammatory activity with minimal side effects is the compound of Example 3; namely, 2-amino-3-(4-chlorobenzoyl)phenylacetamide which was found to have about the same potency as indomethacin but exhibited about only 1/100th as much irritation to the stomach as indomethacin.

The anti-inflammatory activity was demonstrated in laboratory animals using a modification of the Evans-Blue Carrageenan Pleural Effusion Assay of Sancilio, L. F., J. Pharmacol. Exp. Ther. 168, 199–204 (1969).

The compounds of Formula I exhibit inhibition of platelet aggregation in the test method described by Born, J. of Phys. 162, 67–68 p. (1962) and Evans et al., J. of Expt. Med. 128, 877–894 (1968). The test drugs are administered to rats and after two hours the rats are bled and platelet rich plasma obtained. Collagen was added to the platelet rich plasma to induce platelet aggregation and comparisons were made between control and treated samples.

The compounds of Formula I also act as analgetics as determined by the Bradykinin Analgetic Test Method of Dickerson et al., Life Sci. 4, 2063–2069 (1965) as modified by Sancilio and Cheung, Fed. Proc. 35, 774 (1976).

Antipyretic activity of the compounds of Formula I is demonstrated in the lowering of the febrile response in hyperthermic animals without affecting the rectal temperature or normothermic animals. Hyperthermic response produced by subcutaneous injection of Brewer's yeast in rats is overcome by oral administration of as little as 4–8 mg/kg of compounds of Formula I and no significant change in rectal temperature of normothermic rats is observed.

It is an object of the present invention to provide novel compounds and compositions. Another object is to provide a novel method for the treatment of a living animal body and especially mammalian bodies for the purposes of alleviating inflammation and pain, inhibiting blood-platelet aggregation and treating fevers all with a minimum of undesirable side effects in the gastric and intestinal area. Additional objects will become apparent to one skilled in the art and still other objects will become apparent hereinafter.

In the definitions of symbols in the formulas hereof and where they appear elsewhere throughout this specification, the terms have the following significance.

The term "lower alkyl" as used herein includes straight and branched chain radicals of up to eight carbon atoms and is exemplified by such groups as methyl, ethyl, propyl, isopropyl, butyl, sec. butyl, tertiary butyl, amyl, isoamyl, hexyl, heptyl and octyl. The term "lower alkoxy" has the formula —O—lower alkyl.

The term "halogen" when referred to herein includes fluorine, chlorine, bromine and iodine, preferably fluorine, chlorine and bromine.

The term "cycloalkyl" as used herein includes primarily cyclic alkyl radicals containing 3 to 12 carbon atoms inclusive and includes such groups as cyclopropyl, cyclobutyl, cyclopentyl, cyclohexyl, cycloheptyl, and the like.

The term heterocyclic residue refers to radicals such as morpholino, pyrrolidino, piperidino, piperazino, and the like.

DETAILED DESCRIPTION OF THE INVENTION AND PREFERRED EMBODIMENTS

Method of Preparation

The preparation of the compounds of Formula I may be accomplished by reactions which involve the following sequence:

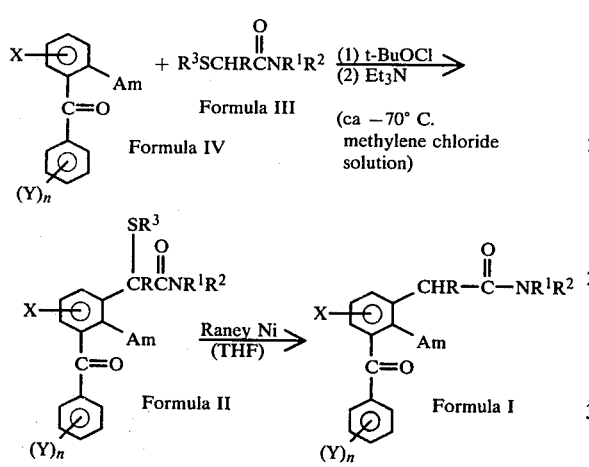

wherein $R$, $R^1$, $R^2$, $X$, $Y$ and $n$ are as hereinabove defined; except $Y$ cannot be lower alkylthio or oxides thereof and $R^3$ is lower alkyl or phenyl. Additionally, compounds wherein $Y$ is —S—alkyl are prepared from compounds of Formula I wherein $Y$ is F (fluorine) by the following reaction sequence:

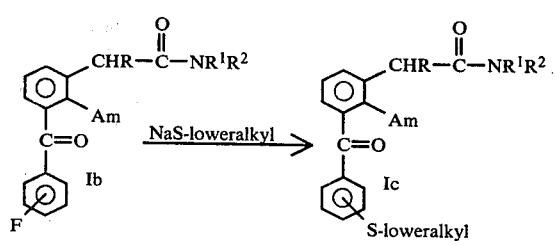

and compounds wherein $Y$ is lower alkyloxythio or lower alkyldioxythio may be prepared by reacting compounds wherein $Y$ is lower alkylthio with 1 or 2 moles of sodium metaperiodate or metachloro perbenzoic acid by the following reaction sequence:

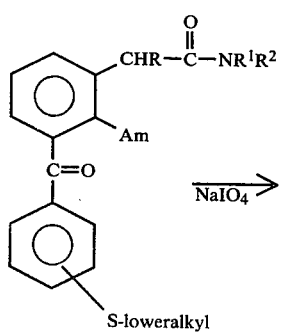

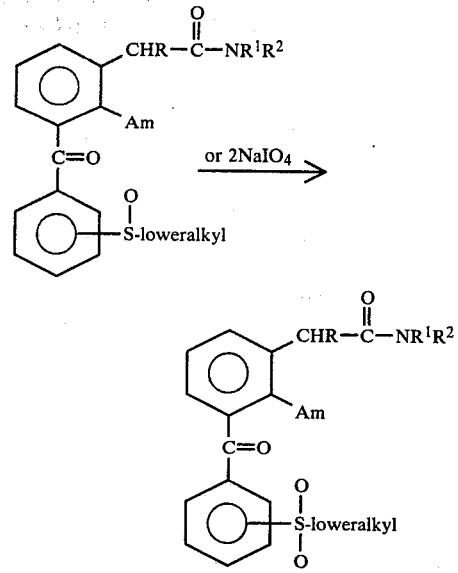

Compounds of Formula I wherein Am is dimethylamino may be prepared by reacting the corresponding 2-amino compound with sodium cyanoborohydride, formaldehyde, acetonitrile and acetic acid.

The preparation of intermediate compounds of Formula II are more fully illustrated in Preparations 6 to 15. Generally, these intermediates are prepared by first reacting the appropriate 2-aminobenzophenones with t-butylhypochlorite and the appropriate thioacetamide in the cold ($-60°$ to $-70°$ C.) followed by addition of triethylamine.

The intermediates of Formula II are reduced with Raney nickel to compounds of Formula I in solvent except when Y=—S—lower alkyl such as tetrahydrofuran and isolated by removing solvent and crystallizing. Compounds of Formula I are prepared as illustrated in the foregoing equation due to interference of Raney Ni on —S—lower alkyl in the reduction step.

PREPARATION 1

4-[2-(Methylthioacetyl)]morpholine

A mixture of 40.2 g (0.3 mole) of ethyl methylthioacetate and 130 g (1.5 mole) of morpholine was heated at reflux for 70 hr. Fractional distillation at reduced pressure gave 45 g (86%) of product b.p. 104°–105° C./0.05 mm Hg. on second distillation.

Analysis: Calculated for $C_7H_{13}NO_2S$: C,47.98; H,7.48; N,7.99. Found: C,47.55; H,7.59; N,8.18.

PREPARATION 2

2-Methylthio-N-methylacetamide

A mixture of 134 g (1.0 mol) of ethyl methylthioacetate and 310 g (10.0 mol) of methylamine was heated in a bomb at 150° C. for 72 hr. The excess amine and the ethanol produced were removed by distillation and the remaining thin syrup was distilled to give 112 g (94%) of the titled compound as a colorless liquid, b.p. 76°–78° C./0.4 mm Hg.

Analysis: Calculated for $C_4H_9NOS$: C,40.31; H,7.61; N,11.75. Found: C,39.78; H,7.69; N,11.88.

PREPARATION 3

2-Methylthio-N,N-dimethylacetamide

A mixture of 134 g (1.0 mol) of ethyl methylthioacetate and 360 g (8.0 mol) of dimethylamine was heated in a bomb at 150° C. for 90 hr. The excess amine and the ethanol produced were removed by distillation and the residue was distilled to give 129 g (97%) of the title compound as a clear colorless liquid, b.p. 76°–77° C./0.5 mm Hg.

Analysis: Calculated for $C_5H_{11}NOS$: C,45.08; H,8.32; N,10.51. Found: C,43.88; H,8.41; N,10.60.

PREPARATION 4

2-(2-Propylthio)acetamide

To a mixture of 46.7 g (0.5 mole) of 2-chloroacetamide in 200 ml of absolute ethyl alcohol was added in a slow stream, a solution of 38.1 g (0.5 mole) of 2-propanethiol in 100 ml of absolute ethyl alcohol and 40 g of 50% aqueous sodium hydroxide. The mixture was heated at reflux for 1 hr., then filtered. The filtrate was concentrated under reduced pressure; the residue was dissolved in methylene chloride and the solution was dried over magnesium sulfate. The mixture was filtered and the filtrate was again concentrated. On standing, the syrupy residue crystallized. Recrystallization from isopropyl ether gave 59.0 g (89%) of white platelets, melting at 52°–54° C.

Analysis: Calculated for $C_5H_{11}NOS$: C,45.08; H,8.32; N,10.51. Found: C,45.05; H,8.32; N,10.55.

PREPARATION 5

2-(1-Propylthio)acetamide

Utilizing the procedure of Preparation 4 but substituting an equal molar amount of 1-propanethiol, there was obtained 61.2 g (92%) of the title compound. The white crystals melted at 49.5°–51.0° C.

Analysis: Calculated for $C_5H_{11}NOS$: C,45.08; H,8.32; N,10.51. Found: C,44.97; H,8.24; N,10.40.

PREPARATION 6

2-Amino-3-benzoyl-5-chloro-α-(methylthio)pentylacetamide

To a cold (−70° C.) solution of 12.77 g (0.055 mole) of 2-amino-5-chlorobenzophenone in 300 ml of methylene chloride, under nitrogen atmosphere, was added 6.0 g (0.552 mole) of t-butylhypochlorite in 20 ml of methylene chloride. After an additional 15 min stirring period, a suspension of 5.8 g (0.055 mole) of α-(methylthio)acetamide in 150 ml of methylene chloride was added. The mixture was stirred at −65° C. for one hour. Triethylamine (5.6 g (0.055 mole)) was added and the solution was allowed to warm to room temperature. The reaction mixture was extracted with several portions of water and the organic layer dried over magnesium sulfate. The volume of solution was reduced in vacuo to about 200 ml and the product crystallized as a yellow solid, m.p. 173.5°–174.5° C. Yield was 6.86 g (37.3%).

Analysis: Calculated for $C_{16}H_{15}N_2O_2SCl$: C,57.40 H,4.52; N,8.37. Found: C,57.38; H,4.50; N,8.51.

PREPARATION 7

2-Amino-3-benzoyl-α-(methylthio)phenylacetamide

To a cold (−70° C.) solution of 19.7 g (0.10 mole of 2-amino-benzophenone in 300 ml of methylene chloride, under nitrogen atmosphere, was added a solution of 11.5 g (0.10 mole) of 95% t-butylpochlorite in 30 ml of methylene chloride followed after 10 min by a solution of 10.5 g (0.1 mole) of methylthioacetamide in 300 ml of tetrahydrofuran. The temperature was maintained at or below −55° C. during these additions. After one additional hour at −60° C. the mixture was allowed to warm to room temperature and the precipitate was collected by filtration. The precipitate was slurried in 200 ml of methylene chloride and 11 g (0.11 mole) of triethylamine was added. The mixture was stirred for 5 min. The solution was washed two times with 100 ml of water and the organic phase dried over magnesium sulfate and concentrated under reduced pressure. The residue was washed with diethylether and dried to yield 13.0 g (43%) of a light yellow powder, m.p. 153°–155° C.

Analysis: Calculated for $C_{16}H_{16}N_2O_2S$: C,63.98; H,5.37; N,9.33. Found: C,63.64; H,5.39; N,9.25.

PREPARATION 8

2-Amino-3-(4-chlorobenzoyl)-α-(phenylthio)-phenylacetamide

To a cold (−70° C.) solution of 34.6 g (0.15 mole) of 2-amino-4'-chlorobenzophenone in 500 ml of methylene chloride was added 17.3 g (0.15 mole) of 95% t-butylhypochlorite, followed after 10 min by a solution of 25.0 g (0.15 mol) of phenylthioacetamide in 400 ml of tetrahydrofuran which was added over a 20 min period. The temperature was maintained at −64° C. or below during these additions. After two hours, 20 g (0.2 mole) of triethylamine was added and the mixture was allowed to warm to room temperature. The mixture was concentrated and the residue partitioned between water and methylene chloride. Material insoluble in either phase was collected by filtration, washed with 20% aqueous ethanol solution and dried to yield 36 g (61%) of light yellow powder, m.p. 189°–191° C.

Analysis: Calculated for $C_{21}H_{17}N_2O_2SCl$: C,63.55; H,4.32; N,7.06. Found: C,63.73; H,4.36; N,7.16.

PREPARATION 9

4-[2-(2-Amino-3-benzoylphenyl)-2-(methylthio)acetyl]-morpholine

To a cold (−65° C.) solution of 9.9 g (0.05 mole) of 2-aminobenzophenone and 8.8 g (0.05 mole) of 4-(α-methylthio)acetylmorpholine in 200 ml of methylene chloride was added dropwise a solution of 5.8 g (0.05 mole) of 95% t-butylhypochlorite in 20 ml of methylene chloride. After one additional hour at −60° C., 5.1 g (0.05 mole) of triethylamine was added and the mixture was allowed to warm to room temperature. The solution was washed two times with 100 ml of water, dried over magnesium sulfate and concentrated under reduced pressure. The residue was chromatographed on 600 g of silica gel eluting first with diisopropylether and finally with 10% acetone in diisopropylether. The eluate was concentrated, the residue dissolved in 150 ml ethanol and the solution poured into 400 ml water. The undissolved solid was collected and crystallized from diethylether and dried. Yield was 12.3 g (62%) of yellow crystals, m.p. 119°–121° C.

Analysis: Calculated for $C_{20}H_{22}N_2O_3S$: C,64.84; H,5.99; N,7.56. Found: C,65.01; H,5.99; N,7.57.

PREPARATION 10

2-Amino-3-benzoyl-5-chloro-α-[(4-chlorophenyl)thio]-phenylacetamide

To a cold (−70° C.) solution of 20 g (0.0863 mole) of 2-amino-5-chlorobenzophenone in 500 ml of methylene chloride under nitrogen atmosphere was added a solution of 9.48 g (0.088 mole) of t-butyl hypochlorite in 50 ml of methylene chloride. After an additional 15 min stirring, a solution of 17.35 g (0.0863 mole) of α-(4-chlorophenylthio)acetamide in 500 ml of a 50/50 mixture of tetrahydrofuran and methylene chloride was added. The mixture was stirred at −70° C. for 2 hr, 8.72 g (0.0863 mole) of triethylamine was added, and the stirred solution was allowed to warm to room temperature over a period of 2 hr. The reaction mixture was extracted with several portions of water and the organic layer dried over magensium sulfate. The volume of liquid was reduced to about 500 ml. Methylene chloride, 500 ml, was added to precipitate the product which after filtration and drying weighed 16.62 g (44.7%). The yellow solid melted at 198°–200° C.

Analysis: Calculated for $C_{21}H_{16}N_2O_2SCl_2$: C,58.48; H,3.74; N,6.49. Found: C,58.49; H,3.77; N,6.67.

PREPARATION 11

2-Amino-3-benzoyl-5-chloro-α-(phenylthio)-phenylacetamide

To a cold (−70° C.) solution of 80.72 g (0.349 mole) of 2-amino-5-chlorobenzophenone in 1.5 liter of methylenechloride, under nitrogen atmosphere, was added 39.1 g (0.360 mole) of t-butyl hypochlorite in 100 ml of methylene chloride. After stirring for 10 min, a solution of 59.1 g (0.354 mole) of α-(phenylthio)acetamide in 1.5 liter of tetrahydrofuran was added. The mixture was stirred for 1.25 hr at −65° C., 37.5 g (0.371 mole) of triethylamine was added and the solution was allowed to warm to room temperature. The reaction mixture was extracted with several portions of water and the organic layer was dried over anhydrous sodium sulfate. The volume of solution was reduced in vacuo and yellow solid precipitated which when recrystallized from acetonitrile was a yellow crystalline solid, m.p. 190°–191° C.(d). Analysis: Calculated for $C_{21}H_{17}N_2O_2SCl$: C,63.55; H,4.32; N,7.06. Found: C,63.62; H,4.29; N,7.08.

PREPARATION 12

2-Amino-3-benzoyl-α-(phenylthio)phenylacetamide

Following the procedure of Preparation 11 but substituting equal molar amounts of 2-aminobenzophenone for 2-amino-5-chlorobenzophenone the title compound was obtained in 57% yield. Recrystallized from methylene chloride-diethyletherhexane, the compound melted at 153°–154° C.

Analysis: Calculated for $C_{21}H_{18}N_2O_2S$: C,69.59; H,5.01; N,7.73. Found: C,69.33; H,5.00; N,7.76.

PREPARATION 13

2-Amino-3-benzoyl-α-(methylthio)-N-methyl-phenylacetamide

A solution of 29.6 g (0.15 mole) of 2-aminobenzophenone in 350 ml of methylene chloride was cooled to −70° C. and 17.9 g (0.15 mol) of 2-methylthio-N-methylacetamide in 20 ml of methylene chloride was added. To the (−70° C.) mixture was added dropwise a solution of 17.2 g (0.15 mole) of 95% t-butylhypochlorite in 30 ml of methylene chloride. The temperature was maintained at or below −65° C. for 1.5 hr, then 15.1 g (0.15 mole) of triethylamine was added rapidly. The solution was allowed to warm to room temperature and was washed with water. The organic solution was concentrated and the residue crystallized when mixed with isopropyl ether. The solid was recrystallized from isopropyl alcohol to give 31 g (65%) of yellow needles, m.p. 149.0°–150.0° C.

Analysis: Calculated for $C_{17}H_{18}N_2O_2S$: C,64.94; H,5.77; N,8.91. Found: C,65.24; H,5.83; N,8.99.

PREPARATION 14

2-Amino-3-benzoyl-α-(methylthio)-N,N-dimethyl-phenylacetamide

A solution of 29.6 g (0.15 mole) of 2-aminobenzophenone in 350 ml of methylene chloride was cooled to −70° C. and 20.0 g (0.15 mole) of 2-methylthio-N,N-dimethylacetamide was added. To the mixture (−70° C.) was added dropwise a solution of 17.2 g (0.15 mole) of 95% t-butylhypochlorite in 30 ml of methylene chloride. The temperature was maintained at or below −65° C. for 1.5 hr, then 15.1 g (0.15 mole) of triethylamine was added rapidly. The solution was allowed to warm to room temperature and was washed with water. The organic solution was concentrated and the residue crystallized when mixed with isopropyl ether. The solid was recrystallized from isoproyl alcohol to give 39.8 g (81%) bright yellow crystals, m.p. 153°–155° C.

Analysis: Calculated for $C_{18}H_{20}N_2O_2S$: C,65.83; H,6.14; N,8.53. Found: C,65.87; H,6.15; N,8.52.

PREPARATION 15

2-Amino-3-(4-fluorobenzoyl)-α-(n-propylthio)-phenylacetamide

A solution of 21.5 g (0.1 mole) of 4'-fluoro-2-aminobenzophenone in 400 ml of methylene chloride was cooled to −70° C. and 11.5 g (0.1 mole) of 95% t-butylhypochlorite was added over a period of 15 min, keeping the temperature below −66° C. To this solution was added a solution of 13.3 g of 2-n-propylthioacetamide in 50 ml of methylene chloride over a 10 min period. The solution was stirred for 1 hr at −65° to −70° C. and then allowed to warm to 0° C. at which point 10.2 g (0.1 mole) of triethylamine was added. The solution was stirred for 10 minutes and then washed with water. The organic solution was dried over magnesium sulfate. After concentrating under reduced pressure, the residue was crystallized from isopropyl alcohol and dried to give 19.5 g (56%) of yellow crystals melting at 140°–142° C.

Analysis: Calculated for $C_{18}H_{19}N_2O_2SF$: C,62.41; H,5.53; N,8.09. Found: C,62.34; H,5.58; N,8.04.

PREPARATION 16

In the same manner as given in Preparation 8,
2-amino-3-(2-fluorobenzoyl)-α-(phenylthio)-phenylacetamide,
2-amino-3-(4-trifluoromethylbenzoyl)-α-(phenylthio)-phenylacetamide,
2-amino-3-(2,4-dichlorobenzoyl)-α-(phenylthio)-phenylacetamide, and
2-amino-3-(2,4-difluorobenzoyl)-α-(phenylthio)-phenylacetamide,
are prepared from phenylthioacetamide, t-butylhypochlorite, and 2-amino-2'-fluorobenzophenone,
2-amino-4'-trifluoromethylbenzophenone,
2-amino-2',4'-dichlorobenzophenone, and
2-amino-2',4'-difluorobenzophenone.

PREPARATION 17

2-Amino-3-benzoyl-5-chloro-α-(methylthio)-N-methyl-phenylacetamide.

To a solution of 38.3 g (0.166 mole) of 2-amino-5-chlorobenzophenone in 1 liter of methylene chloride cooled to −70° C. under an atmosphere of nitrogen was added 18.05 g (0.167 mole) of t-butylhypochlorite. The solution was stirred for 15 min and then a solution of 20.3 g (0.171 mole) of 2-methylthio-N-methylacetamide in 100 ml of methylene chloride was added. The solution was stirred at −70° C. for 2 hrs and 25 ml of triethylamine was added. While stirring, the solution was allowed to warm to room temperature followed by extraction with water and drying of the organic layer with magnesium sulfate. The volume of the solution was reduced to about 400 ml, ether was added and the solution placed in a refrigerator at about 0° C. overnight. The solid which crystallized was dried under high vacuum for about 4 hr at 50° C. Weight of the product was 31.56 g (54.6%) which melted at 170°–171° C.

Analysis: Calculated for $C_{17}H_{17}N_2O_2SCl$: C,58.53; H,4.91; N,8.03. Found: C,58.68; H,4.91; N,8.13.

PREPARATION 18

3-Benzoyl-2-(N-methylamino)-α-(methylthio)-phenylacetamide

When in accordance with the procedure of Preparation 7, 2-N-methylaminobenzophenone is substituted in equimolar amount for 2-aminobenzophenone, the title compound is obtained.

EXAMPLE 1

2-Amino-3-benzoyl-5-chlorophenylacetamide

A mixture of 21.34 g (0.0639 mole) of 2-amino-3-benzoyl-5-chloro-α-(methylthio)-phenylacetamide and excess Raney nickel in a mixture of 900 ml of absolute ethanol and 200 ml of dimethylformamide was stirred at room temperature for 45 min. The mixture was filtered through celite to remove the Raney nickel. The solvent was removed in vacuo to give a yellow solid which when recrystallized melted at 213.5°–215.0° C.(d).

Analysis: Calculated for $C_{15}H_{13}N_2O_3Cl$: C,62.40; H,4.54; N,9.70. Found: C,62.35; H,4.58; N,9.74.

EXAMPLE 2

2-Amino-3-benzoyl-phenylacetamide

To an agitated solution of 9.7 g (0.032 mole) of 2-amino-3-benzoyl-α-(methylthio)-phenylacetamide in 100 ml of tetrahydrofuran was added 80 g of wet Raney nickel (washed 3 times with water and 3 times with tetrahydrofuran). After 10 minutes the mixture was filtered to remove Raney nickel and the filtrate concentrated under vacuum. The residue was crystallized from isopropyl alcohol to give 6.0 g (73%) of yellow needles, m.p. 178.5°–180.0° C.

Analysis: Calculated for $C_{15}H_{14}N_2O_2$: C,70.85; H,5.55; N,11.02. Found: C,70.53; N,5.53; N,11.04.

EXAMPLE 3

2-Amino-3-(4-chlorobenzoyl)phenylacetamide

To an agitated solution of 28.5 g (0.077 mole) of 2-amino-3-(4-chlorobenzoyl)-α-(phenylthio)phenylacetamide in 1 liter of tetrahydrofuran was added 230 g of wet Raney nickel (washed 3 times with water and 3 times with tetrahydrofuran). After 15 minutes the mixture was filtered and the filtrate concentrated under reduced pressure to give 17.4 g (84%) of yellow crystalline solid. Recrystallization from isopropyl alcohol followed by recrystallizing twice from absolute ethanol gave yellow needles, m.p. 212°–215° C.

Analysis: Calculated for $C_{15}H_{13}N_2O_2Cl$: C,62.40; H,4.54; N,9.70. Found: C,62.76; H,4.58; N,9.83.

EXAMPLE 4

4-[2-(2-Amino-3-benzoylphenyl)acetyl]morpholine

To an agitated solution of 18.5 g (0.05 mole) of 4-[2-(2-amino-3-benzoylphenyl)-2-(methylthio)acetyl]morpholine in 300 ml of tetrahydrofuran was added 150 g of wet Raney nickel. After 15 minutes the mixture was filtered and the filtrate concentrated under reduced pressure. After recrystallization of the residue from isopropyl alcohol, there was obtained 13.3 g (82%) of bright yellow crystals, m.p. 156.5°–158.5° C.

Analysis: Calculated for $C_{19}H_{20}N_2O_3$: C,70.35; H,6.22; N,8.64. Found: C,70.24; H,6.21; N,8.63.

EXAMPLE 5

2-Amino-3-benzoyl-N-methylphenylacetamide

A solution of 22.5 g (0.072 mol) of 2-amino-3-benzoyl-α-(methylthio)-N-methylphenylacetamide in 400 ml of tetrahydrofuran was treated with 160 g of wet Raney nickel (washed 3 times with water and 3 times with tetrahydrofuran) for 10 minutes. The mixture was filtered and the filtrate was concentrated. The residue was crystallized from isopropyl alcohol to give 17.2 g (89%) of yellow needles, m.p. 145°–146° C.

Analysis: Calculated for $C_{16}H_{16}N_2O_2$: C,71.62; H,6.01; N,10.44. Found: C,71.76; H,6.05; N,10.52.

EXAMPLE 6

2-Amino-3-benzoyl-N,N-dimethylphenylacetamide

A solution of 33.0 g (0.1 mol) of 2-amino-3-benzoyl-α-(methylthio)-N,N-dimethylphenylacetamide in 500 ml of tetrahydrofuran was treated with 240 g of wet Raney nickel (washed 3 times with water and 3 times with trtrahydrofuran) for 10 minutes. The mixture was filtered and the filtrate was concentrated. The residue was crystallized from isopropyl alcohol to give 27.2 g (96%) of yellow needles, m.p. 123°–124° C.

Analysis: Calculated for $C_{17}H_{18}N_2O_2$: C,72.32; H,6.43; N,9.92. Found: C,72.34; H,6.42; N,9.98.

EXAMPLE 7

2-Amino-3-(4-fluorobenzoyl)-phenylacetamide

A solution of 24.2 g (0.07 mole) of 2-amino-3-(4-fluorobenzoyl)-α-(n-propylthio)phenylacetamide in 300 ml of tetrahydrofuran was treated with 250 g of wet Raney nickel (washed 3 times with water and 3 times with tetrahydrofuran). The mixture was stirred for one hour and filtered. The filtrate was concentrated under vacuum and the residue was recrystallized from 95% ethyl alcohol to give 14.8 g (78%) of yellow needles melting at 184°–186° C.

Analysis: Calculated for $C_{15}H_{13}N_2O_2F$: C,66.17; H,4.81; N,10.29. Found: C,66.32; H,4.81; N,10.48.

EXAMPLE 8

In the same manner as given in Example 2, 2-amino-3-(2-fluorobenzoyl)phenylacetamide, 2-amino-3-(2,4-dichlorobenzoyl)phenylacetamide, 2-amino-3-(2,4-difluorobenzoyl)phenylacetamide, and 2-amino-3-(4-trifluoromethylbenzoyl)phenylacetamide are prepared from
2-amino-3-(2-fluorobenzoyl)-α-(phenylthio)-phenylacetamide,
2-amino-3-(2,4-dichlorobenzoyl)-α-(phenylthio)-phenylacetamide,
2-amino-3-(2,4-difluorobenzoyl)-α-(phenylthio)-phenylacetamide, and
2-amino-3-(4-trifluoromethylbenzoyl)-α-(phenylthio)-phenylacetamide.

EXAMPLE 9

2-Amino-3-(4-methylthiobenzoyl)phenylacetamide

The title compound is prepared by refluxing 2-amino-3-(4-fluorobenzoyl)phenylacetamide with excess sodium methyl mercaptide in ethanol and isolated by suitable means.

EXAMPLE 10

2-Amino-3-(4-oxymethylthiobenzoyl)phenylacetamide

The title compound is prepared by reacting one mole of 2-amino-3-(4-methylthiobenzoyl)phenylacetamide with one mole of sodium metaperiodate and isolated by suitable means.

EXAMPLE 11

2-Amino-3-(4-dioxymethylthiobenzoyl)phenylacetamide

The title compound is prepared by reacting one mole of 2-amino-3-(4-methylthiobenzoyl)phenylacetamide with two moles of sodium metaperiodate and isolated by suitable means.

EXAMPLE 12

2-Amino-3-benzoyl-5-chloro-N-methylphenylacetamide

A solution of 28.33 g (0.081 mole) of 2-amino-3-benzoyl-5-chloro-α-(methylthio)-N-methylacetamide in one liter of tetrahydrofuran was treated with excess Raney nickel at room temperature for 2 hr. The solution was filtered through celite. The Raney nickel residue was washed with acetone and the wash filtered. The combined organic filtrates were dried over magnesium sulfate and the volume reduced to about 300 ml. Excess ether was added and the solution allowed to stand at room temperature for one hr followed by refrigeration overnight. The yellow solid collected and dried weighed 20.94 g (85.68%) and melted at 179°–180° C.

Analysis: Calculated for $C_{16}H_{15}N_2O_2Cl$: C,63.48; H,4.99; N,9.25. Found: C,63.44; H,4.99; N,9.27.

EXAMPLE 13

3-Benzoyl-2-(N-methylamino)-phenylacetamide

When in the procedure of Example 2, 3-benzoyl-2-(N-methylamino)-α-(methylthio)phenylacetamide is substituted for 2-amino-3-benzoyl-α-(methylthio)-phenylacetamide, the title compound is obtained.

EXAMPLE 14

3-Benzoyl-2-(N,N-dimethylamino)-phenylacetamide

A solution of 12.7 g (0.05 mol) of 2-amino-3-benzoyl-phenylacetamide in 150 ml of acetonitrile is treated four times with 16 ml (0.2 mole) of 37% formalin, 6.4 g (0.1 mole) of sodium cyanoborohydride and 2 ml of glacial acetic acid with a 15 minute stirring period between each treatment. The mixture is finally poured into dilute sodium hydroxide and extracted three times with diethylether. The ether extracts are combined, dried over magnesium sulfate and concentrated. The product is isolated by column chromatography.

FORMULATION AND ADMINISTRATION

The present invention also contemplates novel compositions containing the compounds of the invention as active ingredients. Effective quantities of any of the foregoing pharmacologically active compounds may be administered to a living animal body in any one of various ways, for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 250 milligrams or more depending on the size of the animal. For example, a large animal such as a horse may require tablets of 500–1000 mg active ingredient. The unit dosage may be given a suitable number of times daily so that the daily dosage may vary from 0.3 to 450 milligrams. Five to 25 milligrams appears optimum per unit dose.

It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
| --- | --- |
| Active ingredient | 5.0 |
| Lactose | 296.7 |
| Starch | 129.0 |

-continued

| Typical blend for encapsulation | Per capsule, mg. |
|---|---|
| Magnesium stearate | 4.3 |
| Total | 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| | 170.1 mg. |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable—2% sterile solutions.

| | Per cc. |
|---|---|
| Active ingredient | 20 mg. |
| Preservative, e.g., chlorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. The method of producing an inhibitory effect on blood platelet aggregation which comprises administering to a living animal body a blood platelet inhibitory effective amount of a compound having the formula:

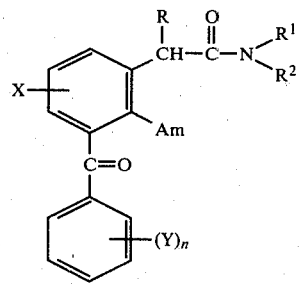

wherein;

R is hydrogen and lower alkyl, $R^1$ and $R^2$ are selected from hydrogen, lower alkyl, cycloalkyl, phenyl and phenyl substituted by lower alkyl, lower alkoxy, halogen, nitro and trifluoromethyl, and $R^1$ and $R^2$ when taken together with the adjacent nitrogen form a heterocyclic residue, X is hydrogen, lower alkyl, lower alkoxy, halogen and trifluoromethyl, Y is hydrogen, lower alkyl, lower alkoxy, halogen, trifluoromethyl, lower alkylthio, lower alkyloxythio or lower alkyldioxythio, Am is primary amino (—$NH_2$), methylamino or dimethylamino, and n is 1–3 inclusive.

2. The method of claim 1 wherein the compound administered is 2-amino-3-benzoyl-5-chlorophenylacetamide.

3. The method of claim 1 wherein the compound administered is 2-amino-3-benzoylphenylacetamide.

4. The method of claim 1 wherein the compound administered is 2-amino-3-(4-chlorobenzoyl)-phenylacetamide.

5. The method of claim 1 wherein the compound administered is 4-[2-(2-amino-3-benzoylphenyl)acetyl]-morpholine.

6. The method of claim 1 wherein the compound administered is 2-amino-3-benzoyl-N-methyl-phenylacetamide.

7. The method of claim 1 wherein the compound administered is 2-amino-3-benzoyl-N,N-dimethyl-phenylacetamide.

8. The method of claim 1 wherein the compound administered is 2-amino-3-(4-fluorobenzoyl)-phenylacetamide.

9. The method of claim 1 wherein the compound administered is 2-amino-3-benzoyl-5-chloro-N-methyl-phenylacetamide.

* * * * *